(12) United States Patent
Bromberg

(10) Patent No.: US 8,006,319 B2
(45) Date of Patent: Aug. 30, 2011

(54) BREAST SELF-EXAM DEVICE

(76) Inventor: Beth Bromberg, Las Vegas, NV (US)

( * ) Notice: Subject to any disclaimer, the term of this patent is extended or adjusted under 35 U.S.C. 154(b) by 673 days.

(21) Appl. No.: 12/009,206

(22) Filed: Jan. 16, 2008

(65) Prior Publication Data

US 2008/0173299 A1    Jul. 24, 2008

Related U.S. Application Data

(60) Provisional application No. 60/881,333, filed on Jan. 19, 2007.

(51) Int. Cl.
*A41D 19/00* (2006.01)
(52) U.S. Cl. .......................................... 2/161.7; 600/587
(58) Field of Classification Search .................. 2/16, 20, 2/21, 161.7, 161.8; 128/95.1, 879, 878, 898; 600/587
See application file for complete search history.

(56) References Cited

U.S. PATENT DOCUMENTS

| | | | | |
|---|---|---|---|---|
| 5,159,717 A * | 11/1992 | Drew et al. | | 2/20 |
| 5,572,744 A | 11/1996 | Reid, Jr. et al. | | |
| 5,873,367 A * | 2/1999 | Buchalter | | 128/898 |
| 5,946,727 A | 9/1999 | Wright et al. | | |
| 6,506,170 B2 | 1/2003 | Morrison | | |
| 7,254,842 B2 * | 8/2007 | Becerra et al. | | 2/161.7 |
| 7,383,592 B2 * | 6/2008 | Nuckols et al. | | 2/161.1 |
| 2006/0090243 A1 | 5/2006 | Becerra et al. | | |

OTHER PUBLICATIONS

Healthwise Incorporated; Nissl, Jan; "Breast Self-Examination"; pp. 1-5; Feb. 22, 2007.
Unicity; "FDA approves "The Touch Enhancing Pad" for breast self-examination"; pp. 1-3; Feb. 1, 2006.
The Wolfe Clinic; Wolfe, Darrell L.; "The Breast Self-Exam Pad"; pp. 1-4; Jan. 1, 2007.
CancerCompass; "Introducing in Touch the New Breast Self-Exam Glove-Ten Minutes a Month Can Save Your Life"; pp. 1-3; Sep. 19, 2006; New York, NY.
International Preliminary Report on Patentability (Jul. 30, 2009).
PCT International Search Report, Jun. 25, 2008.
PCT Written Opinion of International Searching Authority, Jun. 25, 2008.

* cited by examiner

*Primary Examiner* — Katherine Moran
(74) *Attorney, Agent, or Firm* — Robert J. Lauson; Lauson & Tarver LLP

(57) ABSTRACT

A device for breast self-examination worn over the fingers of a user's hand, comprising an operative portion with an outside shell, an inside liner, and a lubricant contained therebetween, and a barrier adhering the outside shell to the inside liner and acting to seal the lubricant within. The operative portion is sized to substantially restrict access to just the pads of the distal and middle regions of the four fingers, preventing the non-recommended use of the thumb and palm during the inspection process, due to their limited sensitivity. The operative portion is designed to allow the recommended substantial lateral displacement of the inside layer relative to the outside shell that remains in substantially immobile contact with an area of skin. The novel design substantially prevents incorrect use thereby increasing the detection effectiveness.

18 Claims, 2 Drawing Sheets

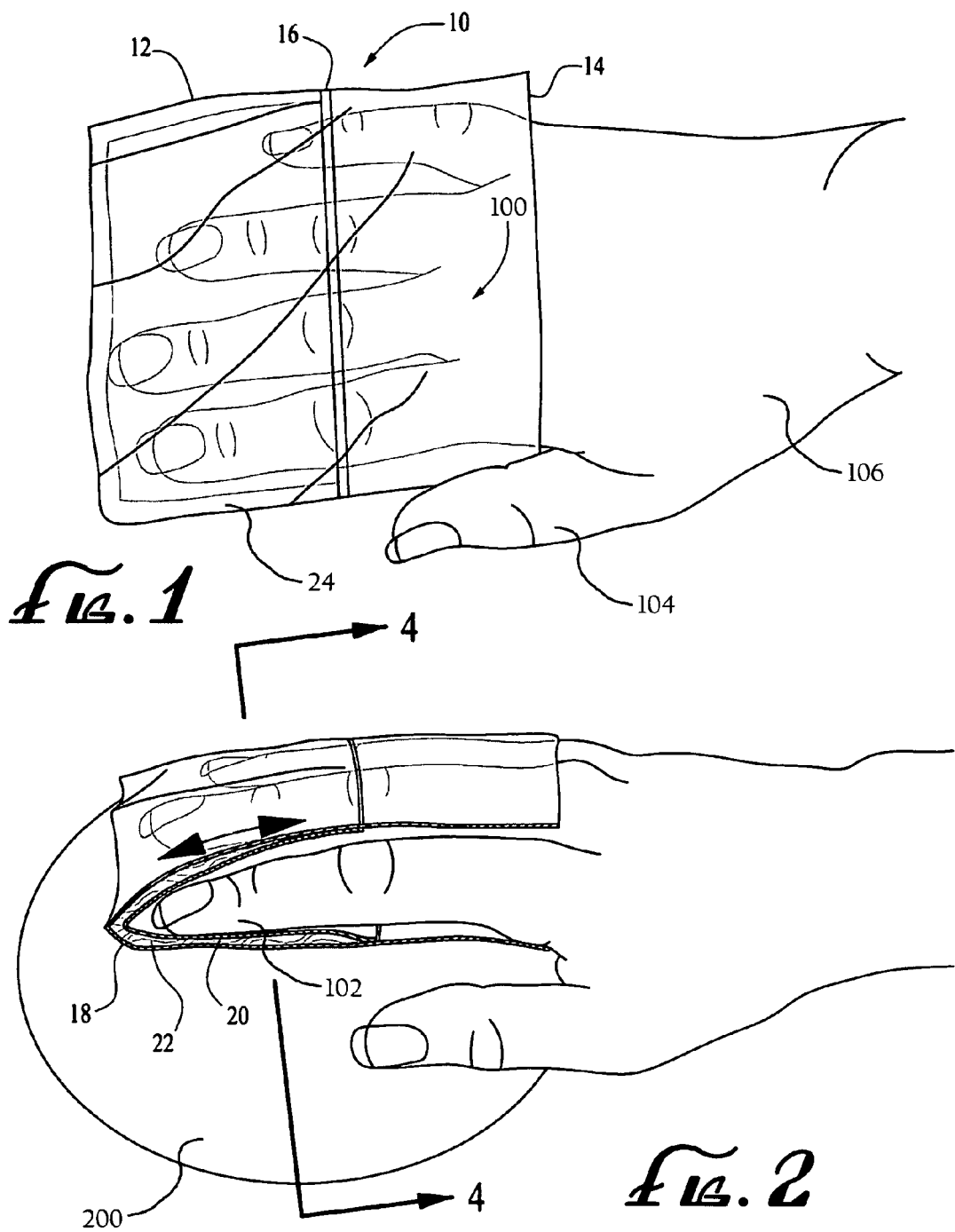

BREAST SELF-EXAM DEVICE

RELATED APPLICATION DATA

This application claims the benefit of U.S. provisional application Ser. No. 60/881,333 filed Jan. 19, 2007.

BACKGROUND OF THE INVENTION

1. Field of the Invention

The present invention relates to an improved device worn on the user's fingertips for enhancing the sense of touch.

2. Description of the Related Art

Pads constructed of thin layers of plastic sheeting with lubricant in between for use as an aid in breast self-examination ("BSE") have been known since at least the mid-1980s. See, e.g. Wright, Perry, U.S. Pat. No. 4,657,021 (Reissue 34,353) and U.S. Pat. No. 4,793,354, those inventors doing business as Inventive Products. The devices are placed over the breast to reduce friction and make very small lumps easier to find than would be possible with a bare hand.

Initially there was some controversy when in 1992 the FDA halted sales of these products, classified as medical devices, until clinical testing was completed. The FDA also wanted to make sure that proper information accompanied the product given the importance of its use for early detection of possible breast cancer. Finally in late 1995 the FDA approved Inventive Products' self-examination breast pad, described as a silicon-filled flexible circular plastic envelope 10 inches in diameter. There remains disagreement among medical experts, however. The U.S. Preventive Services Task Force and the Canadian Task Force on Preventive Health in 2002 and 2003 respectively found no evidence that BSE saves lives and do not recommend the practice. Other organizations endorse these products, including the American Breast Cancer Foundation.

Rates of breast cancer in the U.S. were increasing until recently, and the BSE pads have enjoyed some popularity. Improvements on the pads in the form of large mitts or gloves which encapsulated the user's entire hand came along in the late 1990s and more recently. See, e.g. Wright, U.S. Pat. No. 5,946,727, Morrison U.S. Pat. No. 6,506,170 and Becerra U.S. Publication No. 2006/0090243. Beccerra shows a glove worn over the hand, the fingers divided into separate fingered sections of the glove, and a measure of lubricant sealed beneath each finger. This design tends to limit the lateral displacement of the glove during examination, limiting the effectiveness of the examination. Still, the current BSE products being sold suffer from certain disadvantages and can be improved upon to make the devices more effective and less subject to error in use.

The BSE products for sale now are constructed of two layers with the lubricant in between and a third layer, all the layers tied together around the perimeter of the device but leaving an opening for insertion of the user's hand. The problems with this construction are at least fourfold: 1. the user may tend to do the feeling through their less-sensitive hand rather than their fingertips, using the palm area or thumb; 2. the lubricant may easily bunch up somewhere under the user's hands leaving the compressed area without lubrication; 3. the entire device must be moved when examining breast tissue near the perimeter of the device; and 4. the devices are subject to wear and damage at the perimeter seams which are tied together.

OBJECTS OF THE INVENTION

It is an object of the present invention to provide an improved BSE device that by its very design facilitates proper and most effective use;

It is a further object of the present invention to provide an improved BSE device that keeps the lubricant under the user's finger pads of the proximal area of the fingers;

It is a still further object of the present invention to provide an improved BSE device wherein an inner layer can be slid along for a substantial distance in feeling for tiny lumps without moving the outer layer of the device.

It is a still further object to provide an improved BSE device that cannot be positioned improperly on the user's finger pads; and, It is a still further object to provide an improved BSE device that is durable and can be cleaned as necessary and will last a long time.

These and other objects and advantages of the present invention will become apparent upon reading the following detailed description and upon reference to the accompanying drawings.

SUMMARY OF THE INVENTION

A device for breast self-examination worn over a plurality of fingers of a user's hand, the plurality of fingers having a distal region, a middle region, a proximal region, a metacarpal region, and a finger pad on a palmer side associated with each said plurality of fingers, comprising an operative portion with an outside shell, an inside liner, and a lubricant contained therebetween in a reservoir, the operative portion sized to cover at least a portion of the distal region and up to the middle region, the finger pads contacting an inside surface of the inside liner with the lubricant thereunder, the inside surface being sufficiently small to substantially restrict contact with the inside layer to the finger pads; a barrier adhering the outside shell to the inside liner to define the reservoir and acting to seal the lubricant within the reservoir, the reservoir being sufficiently large to allow substantial lateral displacement of the inside liner by the finger pads while allowing the outside shell to remain in substantially immobile contact with an area of skin.

When referring to parts of the hand, standard anatomical language is used in the specification and claims. From the tip of the fingers towards the wrist, the fingers are divided into the distal, middle, and proximal phalanges. The bones extending from the middle phalanges to the wrist are called metacarpal bones. The top of the hand is called the dorsum; and the bottom is called the palmer surface. The pads are located on the palmer or bottom side of the hand, at the distal, middle, and proximal phalanges. The thumb is an opposable digit, however, having no middle phalanx, it is not considered a finger as described herein.

It has been shown that the most effective portion of the hand for feeling abnormalities in breast tissue are primarily the pads of the fingers on the palmer side in the area of the distal and middle phalanges. The distal and middle pads are areas of heightened sensitivity, and are most capable of feeling minor abnormalities. When referring to fingers in the specification and claims, the thumb is excluded, and the fingers are defined as an index finger, a middle finger, a ring finger, and a little finger of either the left or right hand.

Ineffective areas of the hand include the palm, dorsum or back of the hand, and thumb. Mistakenly using these ineffective areas during an examination can create a false sense of security that the BSE is being used effectively, potentially causing an abnormality to be missed. Therefore, the design of the present device substantially restricts the user to the use of the pad of the fingers in the distal or middle region, increasing the effective use for even the least experienced users, thereby increasing the chance of discovering an abnormality, if present in the tissue.

Additionally, the reservoir in the operative region needs to be large enough to allow a substantial lateral displacement during the inspection process. Therefore, even though the operative region is restricted in width to approximately the distal and middle regions of the fingers, there is plenty of room for the inside liner to move laterally relative to the outside liner. To further improve the effectiveness and lateral displacement of the present invention, optionally the outside shell and inside liner can both be pouch shaped, the lubricant being deposited within the outside shell, the inside liner being nested within the outside shell, a lip of the inside liner being adhered to outside shell to form the reservoir, the lubricant being sealed within the reservoir reducing the coefficient of friction between the outside shell and inside liner during lateral displacement.

Also, optionally, the outside shell and the inside liner can be seamless in construction in at least the operative portion, allowing substantial lateral displacement without tactile interference. Without seams, the user may take larger may feel with larger sweeps or circular motions without the interference of a seam. A seam may hide beneath it an abnormality that would otherwise be sensed using the seamless design of the present invention.

The device may further comprise an extension portion extending from the barrier to at least the proximal region and up to the metacarpal region of the plurality of fingers and serving to further secure the device over the plurality of fingers. Although this extension portion is not critical to the use of the device, it can aid in maintaining the position of the device on the user's fingers, substantially preventing it from falling off during use. This extension portion can be simply a continuation of the outside shell, being made from a continuous material, or a continuation of the inside liner, being made from a continuous material.

The operative portion may also encompass the plurality of fingers including a dorsum or back side and the palm or palmer side, so that the device is properly fitted over the plurality of fingers regardless of the device's orientation, allowing the finger pads to be in contact with the inside surface with the lubricant thereunder. It is important to have a device that is properly positioned and ready for use regardless of the orientation of the hand, being either palm side or back side up. The user will be able to focus on the important examination task at hand, rather than the positioning of the glove.

It is additionally important to optimally size the reservoir to provide the lateral displacement necessary for proper inspection while maintaining a limited volume reservoir that is appropriately sized to maintain a layer of the lubricant underneath the finger pads, substantially preventing the lubricant from being completely displaced to an unused portion. In a large reservoir, it is possible that the area under the finger pads will be under lubricated, while the lubricant resides uncompressed portions of the reservoir. The design of the present invention allows for optimal lateral displacement while maintaining an appropriate quantity of lubricant under the fingers.

Material choice and thickness for the inside liner and outside shell are very important. A material should allow the user to feel small lumps without obscuration, while being substantially non-reactive and hypoallergenic. A preferred material for the outside shell and the inside liner is a urethane material, sufficiently thin to allow detection of lumps, unusual thicknesses, or abnormal changes in an underlying tissue.

A device for breast self-examination worn over a plurality of fingers of a user's hand, the plurality of fingers having a distal region, a middle region, a proximal region, a metacarpal region, and a finger pad on a palmer side associated with each said plurality of fingers, comprising an outside shell being pouch shaped; a lubricant being deposited in the outside shell; and an inside liner being pouched shaped and nested within the outside shell, a lip of the inside liner being adhered to outside shell to form a barrier and defining a reservoir, the lubricant being sealed within the reservoir creating an operative portion sized to receive at least the distal portion of the plurality of fingers while substantially excluding a palm portion and a thumb portion.

A sufficient amount of the lubricant is included to sufficiently coat the reservoir, thereby reducing the coefficient of friction between the outside shell and inside liner during lateral displacement regardless of the device's orientation relative to the plurality of fingers inserted therein.

A method for using a device for breast self-examination comprising the steps of providing a device including an operative portion with an outside shell, an inside liner, and a lubricant sealed therebetween; inserting into the device a plurality of fingers, each of the plurality of fingers having a distal portion with a finger pad; placing the device on an area of skin with the outside shell contacting the area of skin; and displacing substantially in a lateral manner the inside liner with the finger pad of each of the plurality of fingers while the outside shell remains in substantially immobile contact with the area of skin; thereby detecting lumps, unusual thicknesses, or abnormal changes in an underlying tissue through the advantageous use of the heightened sensitivity of the finger pads. A further optional step may include restricting substantially contact with the operative portion to the distal portion of the plurality of fingers; or excluding substantially from the operative portion a palm portion and a thumb portion.

BRIEF DESCRIPTION OF THE SEVERAL VIEWS OF THE DRAWINGS

FIG. 1 is a top perspective view of the preferred embodiment of the present invention placed on the user's right hand;

FIG. 2 is a side perspective view of the preferred embodiment with a section cut away;

Figure 3:
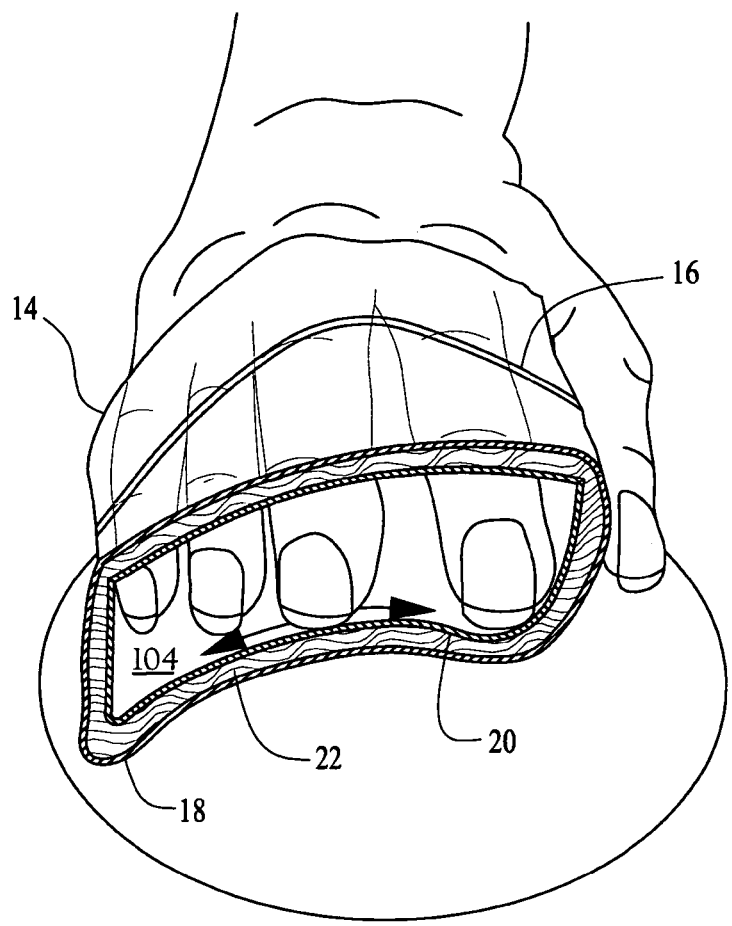
FIG. 3 is a front perspective view of the preferred embodiment, again with a section cut away; and, FIG. 4 is a sectional view of the preferred embodiment as indicated.

LISTING OF REFERENCE NUMERALS OF FIRST-PREFERRED EMBODIMENT device 10
operative portion 12
extension portion 14
barrier 16
outside shell 18
inside liner 20
lubricant 22
reservoir 24
inside surface 26
fingers 100
finger pad 102
thumb 104
hand 106
area of skin 200
underlying tissue 202

DESCRIPTION OF THE PREFERRED EMBODIMENTS

Referring first to FIG. 1, a breast self-examination or BSE device 10 is shown. The device 10 is just large enough to cover the user's fingers, and includes an operative portion 12 and an extension portion 14, and a barrier or dam 16 between the two.

Figure 4:
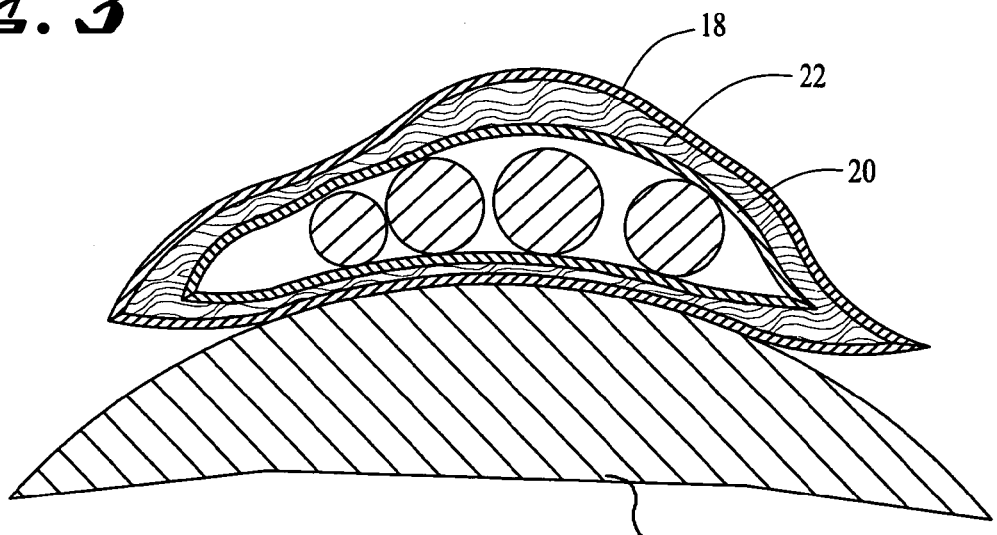

As better seen in FIGS. 2-4, the operative portion 12 includes an outside layer or shell 18, an inside layer or liner 20 and lubricant 22 between the two, held within a reservoir 24. The outside shell 18 and inside liner 16 are only tied together at the barrier 16. The barrier 16 can be created by heat sealing or other known adhering means or method. The extension portion 14 is preferably a continuation of the outside shell 18 of the device 10 although other constructions are possible, such as an extension of the inside liner 20 or no extension at all.

The material for the outside shell 18 and inside liner 16 is preferably PS 7010 urethane material, gauge 0.0025 inches, natural or clear color, available from Deerfield Urethane, Inc., S. Deerfield Mass. The lubricant 22 is USP mineral oil available from Cumberland Swan, Smyrna, Tenn.

Having described the improved BSE device 10, it is now possible to discuss its function and use. In general, like the prior art devices, the fluid between the layers decreases kinetic or moving friction such that even very small lumps, down to the size of a grain of salt, are exaggerated and can be felt by the user when the device is properly used.

The user places the device 10 over her fingers 100, the operative portion 12 extending from the tips of the fingers 100 down to at least the distal region; the extension portion 14 extending down to at least the proximal region of the fingers 100, and the finger pads contacting the inside surface 26. The thumb 12 and palm are substantially excluded from contacting the operative portion 12. Because the device is one layer 20 inside the other 18 outside with the lubricant 22 all the way around the user's fingers 100, it is not possible to put it on incorrectly, such that the two layers 18, 20 and lubricant 22 will always be below the user's finger pads 102. Moreover, the barrier or dam 16 ensures the lubricant 22 will always be around the user's distal and middle regions of the fingers 100 and not bunched under the palm of the user's hand 106.

Then the finger pads 102 and device 10 are placed over an area of skin 200 of the breast tissue, and the user moves the inside liner 20 while keeping the outside shell 18 stationary. Because the inside liner 18 is not tied to the outside shell 20 around the perimeter of the device 10, except at the barrier 16, in the area around the user's finger pads in the distal region it is possible to move the inside liner 20 a substantial distance, enabling detection of abnormalities in underlying tissue 202. The specific instructions and best techniques to use in doing the examination, when during the month to do it, standing up and/or lying down, vertical, horizontal and or small, circular or spiral patterns, etc., can be found on various websites, e.g. www.webmd.com/hw/healthy_women/hw3791.asp.

Moreover, the device 10 is easy to manufacture and its construction lends itself to being simple to clean as necessary and durable and long lasting. Since the inner liner 20 is not stitched or sealed to the outer shell 18 around the perimeter, the entire inner liner 20 can be pulled out and gently washed off and any debris easily removed.

While particular forms of the invention have been illustrated and described, it will also be apparent to those skilled in the art that various modifications can be made without departing from the spirit and scope of the invention. Accordingly, it is not intended that the invention be limited except by the claims.

What is claimed is:

1. A device for breast self-examination worn over a plurality of fingers of a user's hand, the plurality of fingers having a distal region, a middle region, a proximal region, a metacarpal region, and a finger pad on a palmer side associated with each of said plurality of fingers, said device comprising:
   an operative portion with an outside shell, an inside liner, and a lubricant contained therebetween in a reservoir, the operative portion sized to cover at least a portion of the distal regions and up to the middle regions of the plurality of fingers, the finger pads contacting an inside surface of the inside liner with the lubricant thereunder, the inside surface being sufficiently small to substantially restrict contact with the inside layer to the finger pads; and
   a barrier adhering the outside shell to the inside liner to define the reservoir and acting to seal the lubricant within the reservoir, the reservoir being sufficiently large to allow substantial lateral displacement of the inside liner by the finger pads while allowing the outside shell to remain in substantially immobile contact with an area of skin, the inside liner being peripherally unattached to the outside shell below the barrier, the barrier extending about an entry sized to receive the plurality of fingers into the operative portion; and,
   an extension portion extending from the barrier and forming an upper opening to admit the plurality of fingers therethrough, the upper opening substantially corresponding in size to the entry of the operative portion for collective insert of the plurality of fingers.

2. The device of claim 1 wherein the extension portion extends from the barrier to at least the proximal region and up to the metacarpal region of the plurality of fingers and serving to further secure the device over the plurality of fingers.

3. The device of claim 1 wherein the operative portion encompasses the plurality of fingers including a dorsum side and the palmer side, so that the device is properly fitted over the plurality of fingers regardless of the device's orientation, allowing the finger pads to be in contact with the inside surface with the lubricant thereunder.

4. The device of claim 1 wherein the outside shell and the inside liner are both seamless in the operative portion, allowing substantial lateral displacement without tactile interference.

5. The device of claim 1 wherein the extension portion is a continuation of the outside shell, being made from a continuous material.

6. The device of claim 1 wherein the extension portion is a continuation of the inside liner, being made from a continuous material.

7. The device of claim 1 wherein the lubricant is a USP mineral oil.

8. The device of claim 1 wherein the outside shell and the inside liner are made of a urethane material sufficiently thin to allow detection of lumps, unusual thicknesses, or abnormal changes in an underlying tissue.

9. The device of claim 1 wherein the reservoir of the operative area is appropriately sized to maintain a layer of the lubricant underneath the finger pads, substantially preventing the lubricant from being completely displaced to an unused portion.

10. The device of claim 1 wherein the outside shell and inside liner are both pouch shaped, the lubricant being deposited within the outside shell, the inside liner being nested within the outside shell, the lubricant being sealed within the reservoir reducing the coefficient of friction between the outside shell and inside liner during lateral displacement.

11. The device of claim 10 wherein the outside shell and the inside liner are seamless in construction in at least the operative portion, allowing substantial lateral displacement without tactile interference.

12. A device for breast self-examination worn over a plurality of fingers of a user's hand, the plurality of fingers having a distal region, a middle region, a proximal region, a metacarpal region, and a finger pad on a palmer side associated with each said plurality of fingers, said device comprising:
- an outside shell being pouch shaped;
- an inside liner being pouched shaped and nested within the outside shell, a lubricant being deposited between the outside shell and the inside liner;
- a barrier and sealing a reservoir about the inside liner, the lubricant being sealed within the reservoir creating an operative portion sized to receive the distal portions of the plurality of fingers while substantially excluding a palm portion and a thumb portion, the inside liner being peripherally unattached to the outside shell below the barrier, the barrier extending about an entry sized to receive the plurality of fingers into the operative portion; and,
- an extension portion extending from the barrier and forming an upper opening to admit the plurality of fingers therethrough, the upper opening substantially corresponding in size to the entry of the operative portion for collective insert of the plurality of fingers.

13. The device of claim 12 further comprising an extension portion formed by the continuation of the outside shell beyond the barrier, the extension portion covering at least the proximal region and up to the metacarpal region of the plurality of fingers and serving to further secure the device over the plurality of fingers.

14. The device of claim 12 wherein a sufficient amount of the lubricant is included to sufficiently coat the reservoir thereby reducing the coefficient of friction between the outside shell and inside liner during lateral displacement regardless of the device's orientation relative to the plurality of fingers inserted therein.

15. The device of claim 12 wherein the outside shell and inside liner are both seamless in the operative portion, allowing substantial lateral displacement without tactile interference.

16. A method for breast self-examination comprising the steps of:
- providing a device including an operative portion with an outside shell, an inside liner, and a lubricant sealed therebetween by a barrier, the device including an extension portion extending from the barrier, the inside liner being peripherally unattached to the outside shell below the barrier, the barrier extending about an entry sized to receive a plurality of fingers into the operative portion, the extension portion forming an upper opening to admit the plurality of fingers therethrough, the upper opening substantially corresponding in size to the entry of the operative portion for collective insert of the plurality of fingers;
- inserting the plurality of fingers into the inside liner of the device, each of the plurality of fingers having a distal portion with a finger pad;
- placing the device on an area of skin with the outside shell contacting the area of skin; and
- displacing substantially in a lateral manner the inside liner with the finger pad of each of the plurality of fingers while the outside shell remains in substantially immobile contact with the area of skin;
- thereby detecting lumps, unusual thicknesses, or abnormal changes in an underlying tissue through the advantageous use of the heightened sensitivity of the finger pads.

17. The method of claim 16 further comprising the step of:
- restricting substantially contact with the operative portion to primarily the distal portion of the plurality of fingers.

18. The method of claim 16 further comprising the step of:
- excluding substantially from the operative portion a palm portion and a thumb portion.

* * * * *